US009189083B2

(12) United States Patent
Roche et al.

(10) Patent No.: US 9,189,083 B2
(45) Date of Patent: *Nov. 17, 2015

(54) METHOD AND SYSTEM FOR MEDIA PRESENTATION DURING OPERATIVE WORKFLOW

(75) Inventors: Martin Roche, Fort Lauderdale, FL (US); Jason McIntosh, Sugar Hill, GA (US); Marc Boillot, Plantation, FL (US); Carlos Gil, Hallandale Beach, FL (US)

(73) Assignee: ORTHOSENSOR INC., Dania Beach, FL (US)

( * ) Notice: Subject to any disclaimer, the term of this patent is extended or adjusted under 35 U.S.C. 154(b) by 732 days.

This patent is subject to a terminal disclaimer.

(21) Appl. No.: 13/277,408

(22) Filed: Oct. 20, 2011

(65) Prior Publication Data

US 2012/0035868 A1    Feb. 9, 2012

Related U.S. Application Data

(63) Continuation-in-part of application No. 12/050,790, filed on Mar. 18, 2008, now Pat. No. 8,060,841.

(60) Provisional application No. 61/498,647, filed on Jun. 20, 2011.

(51) Int. Cl.
| | |
|---|---|
| *G06F 3/03* | (2006.01) |
| *A61B 8/00* | (2006.01) |
| *G06Q 50/22* | (2012.01) |
| *G06F 3/043* | (2006.01) |
| *G06F 3/0346* | (2013.01) |

(52) U.S. Cl.
CPC ............ *G06F 3/0325* (2013.01); *A61B 8/4245* (2013.01); *G06Q 50/22* (2013.01); *G06F 3/0346* (2013.01); *G06F 3/043* (2013.01)

(58) Field of Classification Search
CPC ..... G06F 3/0325; G06F 3/043; G06F 3/0346; G06Q 50/22; A61B 8/4245
See application file for complete search history.

(56) References Cited

U.S. PATENT DOCUMENTS

| | | | |
|---|---|---|---|
| 5,274,363 A | | 12/1993 | Koved |
| 5,995,450 A | * | 11/1999 | Cole et al. ..................... 367/138 |
| 6,069,594 A | * | 5/2000 | Barnes et al. ..................... 345/7 |
| 6,090,114 A | | 7/2000 | Matsuno et al. |
| 6,130,663 A | | 10/2000 | Null |
| 6,137,427 A | | 10/2000 | Binstead |
| 6,313,825 B1 | | 11/2001 | Gilbert |

(Continued)

OTHER PUBLICATIONS

Wickline A., "Helping to Make Total Knee Replacement Even Better", St. Elizabeth Medical Center, Brochure, p. 1-2. http://www.geneseeortho.com/pdfs/kneebroch.pdf.

(Continued)

*Primary Examiner* — Andrew Schechter
*Assistant Examiner* — Alexander Satanovsky

(57) ABSTRACT

A portable measurement system is provided comprising a probe, two trackers, a receiver and a pod. A user interface control captures a location and position of the probe in a three-dimensional sensing space with respect to a coordinate system of the receiver from time of flight waveform analysis. The system suppresses a ringing portion of the received ultrasonic and minimizes distortion associated with ultrasonic transducer ring-down during high-resolution position tracking of the probe and the two trackers. Media is presented according to a customized use of the probe and two trackers during an operation workflow.

12 Claims, 7 Drawing Sheets

(56) References Cited

U.S. PATENT DOCUMENTS

| | | |
|---|---|---|
| 6,546,277 B1 | 4/2003 | Franck et al. |
| 6,937,227 B2 | 8/2005 | Qamhiyah |
| 7,078,911 B2 | 7/2006 | Cehelnik |
| 7,081,884 B2 | 7/2006 | Kong |
| 7,092,109 B2 | 8/2006 | Satoh |
| 7,130,754 B2 | 10/2006 | Satoh |
| 7,139,418 B2 | 11/2006 | Abovitz et al. |
| 7,309,339 B2 | 12/2007 | Cusick et al. |
| 7,392,076 B2 | 6/2008 | Moctezuma de La Barrera |
| 7,395,181 B2 | 7/2008 | Foxlin |
| 7,477,926 B2 | 1/2009 | McCombs |
| 7,559,931 B2 | 7/2009 | Stone |
| 7,604,645 B2 | 10/2009 | Barzell et al. |
| 7,636,595 B2 | 12/2009 | Marquart et al. |
| 7,643,862 B2 * | 1/2010 | Schoenefeld ............. 600/407 |
| 7,657,298 B2 | 2/2010 | Moctezuma de la Barrera et al. |
| 7,660,623 B2 | 2/2010 | Hunter et al. |
| 7,681,448 B1 | 3/2010 | Preston et al. |
| 7,685,861 B2 | 3/2010 | Lynch et al. |
| 7,689,032 B2 | 3/2010 | Strassenburg-Kleciak |
| 7,771,436 B2 | 8/2010 | Moctezuma De La Barrera et al. |
| 7,824,328 B2 | 11/2010 | Gattani et al. |
| 2001/0011175 A1 | 8/2001 | Hunter et al. |
| 2002/0087075 A1 * | 7/2002 | Bucholz ................. 600/429 |
| 2003/0132913 A1 | 7/2003 | Issinski |
| 2004/0024309 A1 | 2/2004 | Ferre et al. |
| 2004/0236424 A1 | 11/2004 | Berez et al. |
| 2004/0254584 A1 | 12/2004 | Sarin et al. |
| 2005/0256689 A1 * | 11/2005 | Schulz ................. 703/11 |
| 2006/0058615 A1 * | 3/2006 | Mahajan et al. ........... 600/407 |
| 2006/0092022 A1 | 5/2006 | Cehelnik |
| 2006/0161871 A1 | 7/2006 | Hotelling |
| 2006/0164241 A1 | 7/2006 | Makela |
| 2006/0224429 A1 | 10/2006 | Mathew |
| 2006/0235420 A1 | 10/2006 | Irving |
| 2006/0256090 A1 | 11/2006 | Huppi |
| 2007/0127039 A1 | 6/2007 | Njolstad |
| 2007/0175489 A1 | 8/2007 | Moctezuma De La Barrera et al. |
| 2007/0266791 A1 * | 11/2007 | Nakamura ................. 73/627 |
| 2008/0269599 A1 | 10/2008 | Csavoy et al. |
| 2009/0287089 A1 * | 11/2009 | Spector ................. 600/466 |
| 2009/0318836 A1 | 12/2009 | Stone et al. |
| 2010/0063508 A1 | 3/2010 | Borja et al. |
| 2010/0069911 A1 | 3/2010 | Borja et al. |
| 2010/0076505 A1 | 3/2010 | Borja et al. |
| 2010/0137869 A1 | 6/2010 | Borja et al. |
| 2010/0160771 A1 | 6/2010 | Gielen et al. |
| 2010/0210939 A1 | 8/2010 | Hartmann et al. |
| 2012/0022546 A1 * | 1/2012 | Hubschman et al. ......... 606/107 |
| 2012/0209117 A1 * | 8/2012 | Mozes et al. ............. 600/439 |

OTHER PUBLICATIONS

Edwards, S.,"Stryker Navigation System", Baystate Medical Center, Brochure, p. 1-7. http://www.baystatehealth.org/StaticFiles/Baystate/Services/Surgery/Surgery%20at%20BMC/Hip%20and%20Knee%20Replacement/Computer-assisted%20Surgery/Stryker/Stryker.pdf.

Kang. M, "Early Clinical Results Show High Degree of Accuracy and Ease-of-Use KneeAlign Surgical Navigation System", CAOS Meeting, Paris, France, Jun. 19, 2010. http://www.orthalign.com/corporate/news/2010/2010JUN21.asp.

Computer Assisted Surgical Navigational Orthopedic Procedures, BlueCross BlueShield of North Carolina, Oct. 2004, Corporate Medical Policy http://www.bcbsnc.com/assets/services/public/pdfs/medicalpolicy/computer_assisted_surgical_navigational_orthopedic_procedures.pdf.

Computer-assisted Musculoskeletal Surgical Navigational Orthopedic Procedure, BlueCross BlueShield of Minnesotta, Medical and Behavioral Health Policy Manual, Medical and Beh http://notes.bluecrossmn.com/web/medpolman.nsf/50c2d5c81dd37e6a862569bd0054c1b2/f9c0a3e1697cd345862575bb007dea7d/$FILE/Computer-Assisted%20Musculoskeletal%20Surgical%20Navigat.

S. Parratte et. al., "Effect of Postoperative Mechanical Axis Alignment on the Fifteen-Year Survival of Modern, Cemented Total Knee Replacements" 2010;92:2143-9, Journal of http://www.sfhga.com/usr/Deane%20Gladem/Postop%20Mechanical%20Axis%20Alignment,%20Cemented%20Knee.pdf.

"Medical Necessity Guidelines, Knee Arthroplasty", CareAllies, No. 0347, May 15, 2007 http://www.careallies.com/pdf/ex198_knee_arthroplasty.pdf.

F.W. Werner et. al. "The effect of valgus/varus malalignment on load distribution in total knee replacements", Journal of Biomechanics 38 (2005) 349-355 http://www.engr.ku.edu/~kubiomech/ejbrl/PDF/JOURNALS/JB_38_2.pdf.

R. Nabeyama et al., "The accuracy of image-guided knee replacement based on computed tomography", 2004;86-B:366-71, Journal of Bone & Joint Surgery http://web.jbjs.org.uk/cgi/content/abstract/86-B/3/366.

Mont, M.A., "Effect of postoperative Mechanical Axis Alignment . . . " Commentary & Perspective, Sep. 15, 2010,http://commentary.jbjs.org/index.php/2010/09/148/.

Heck D.A., Computer Assisted Surgery (CAS), Baylor Health Care System, Slide Presentation http://www.nist.gov/el/isd/upload/Connputer_Assisted_Surgery_Heck.pdf.

* cited by examiner

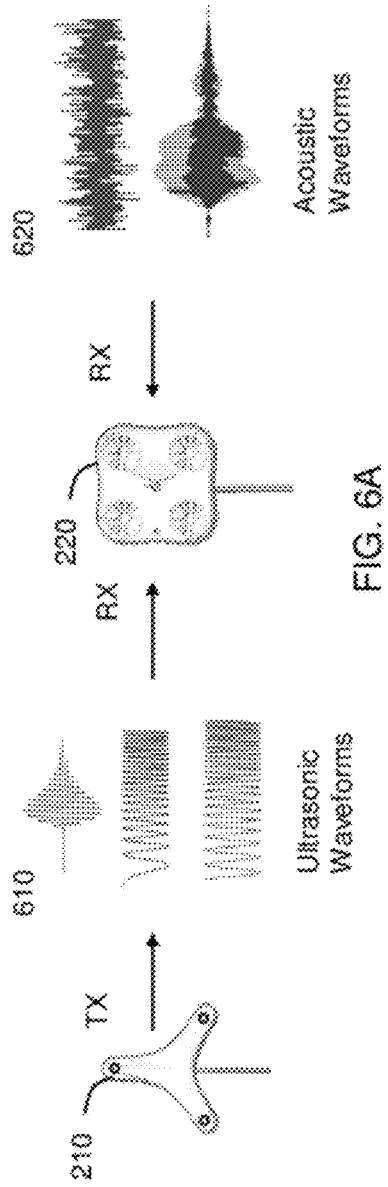
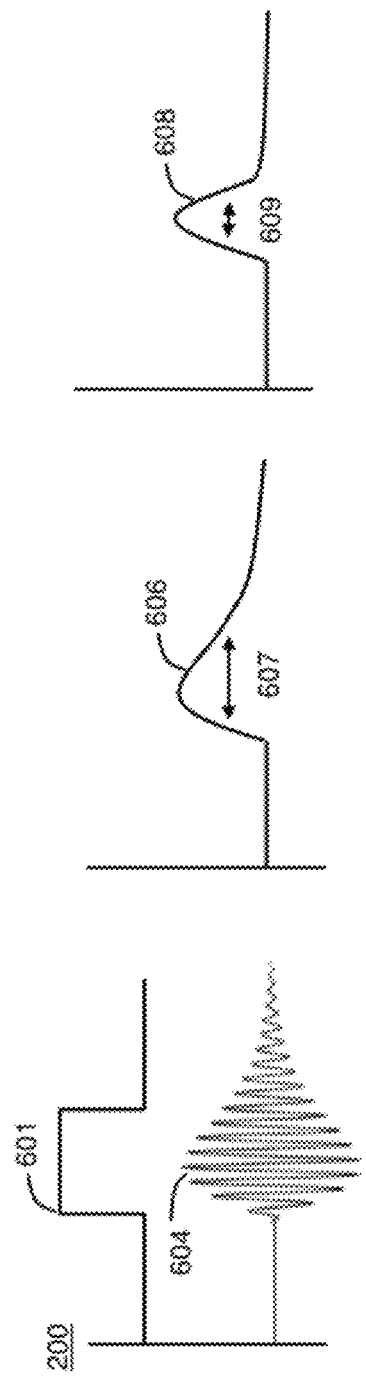
FIG. 6A
FIG. 6B

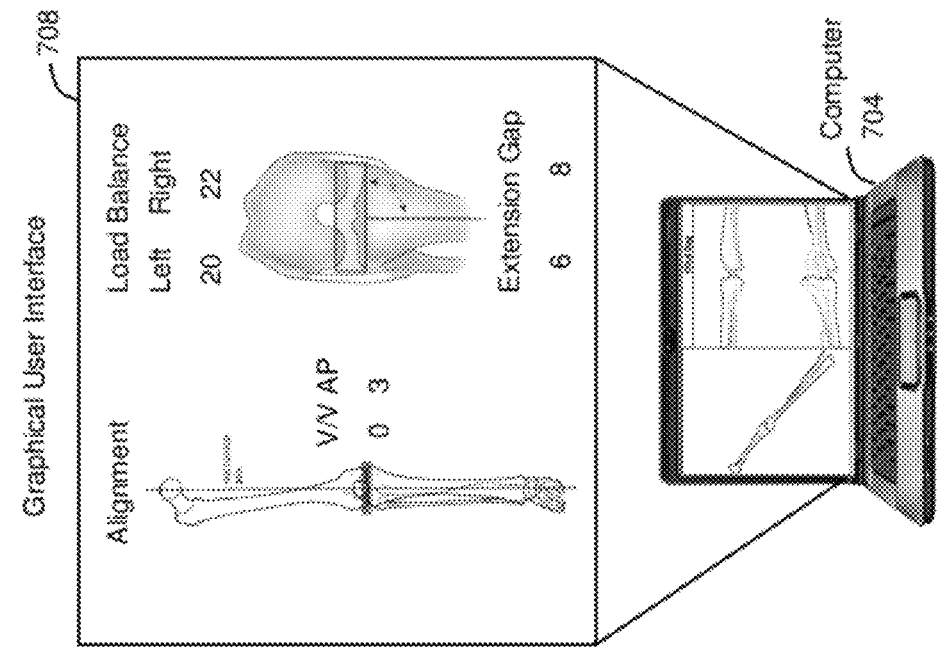
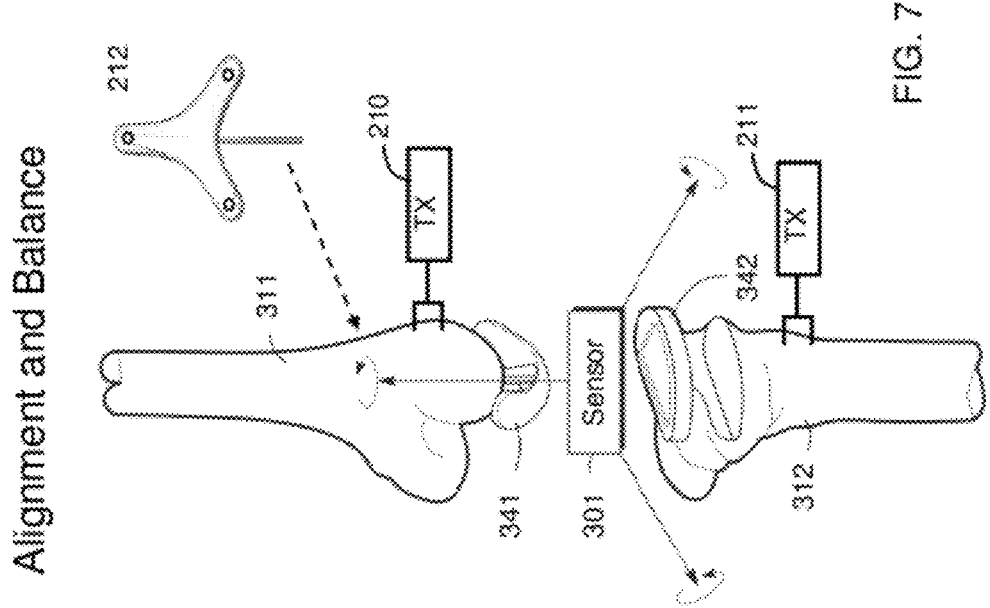
FIG. 7

METHOD AND SYSTEM FOR MEDIA PRESENTATION DURING OPERATIVE WORKFLOW

CROSS-REFERENCE TO RELATED APPLICATION

This application is a Continuation-In-Part of U.S. patent application Ser. No. 12/050,790 filed on Mar. 18, 2008. This application also claims the priority benefit of U.S. Provisional Patent Application No. 61/498,647 filed on Jun. 20, 2011, the entire contents of which are hereby incorporated by reference.

BACKGROUND

1. Field

The present disclosure relates generally to medical interface devices, and more specifically to electronics for orthopedic instrumentation and measurement.

2. Introduction

Clinicians rely on information during an operative workflow. Such media may be in various visual and auditory formats. As sophisticated instruments are introduced in the clinical environment, clinicians may experience a learning curve for user interface applications.

A need exists for customizing the user experience to facilitate instrument use during operative workflow.

BRIEF DESCRIPTION OF THE DRAWINGS

FIG. 6A depicts communication between exemplary components of the orthopedic tracking system in accordance with one embodiment;

FIG. 6B illustrates signal processing of the communication in FIG. 6A in accordance with one embodiment; and FIG. 7 depicts an orthopedic alignment and balance GUI in accordance with one embodiment.

DETAILED DESCRIPTION

Figure 1:
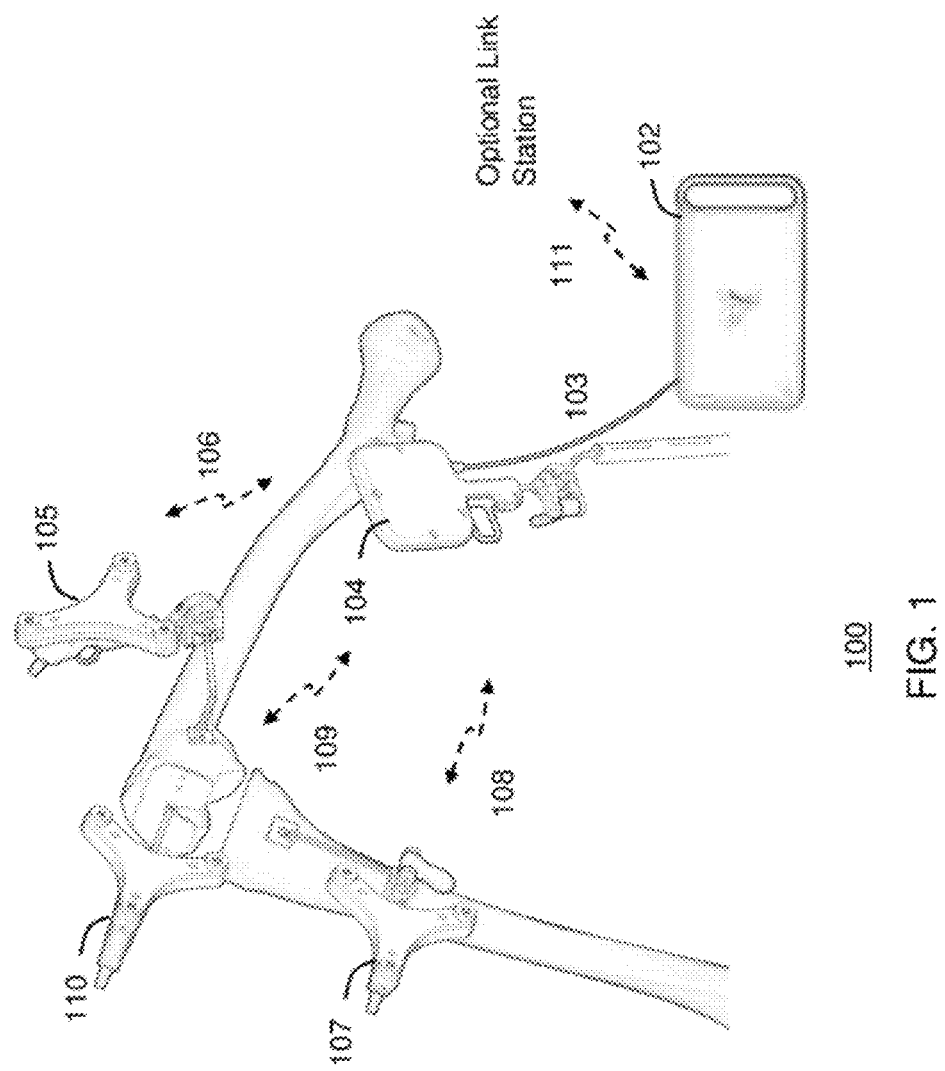
FIG. 1 depicts an orthopedic tracking system in accordance with one embodiment.

While the specification concludes with claims defining the features of the invention that are regarded as novel, it is believed that the invention will be better understood from a consideration of the following description in conjunction with the drawing figures, in which like reference numerals are carried forward.

In one embodiment, a computer readable storage medium, comprises computer instructions for directing a controller to perform the steps of emitting ultrasonic waveforms on a probe in a three-dimensional sensing space, digitally sampling ultrasonic waveforms on a receiver to produce sampled received ultrasonic waveforms, tracking a relative location and movement of the probe in the three-dimensional ultrasonic sensing space from differential time of flight waveform analysis of the sampled received ultrasonic waveform, suppressing a ringing portion of the received ultrasonic waveforms that overlap with digitally sampled acoustic waveforms received at the microphones, and minimizing a distortion associated with ultrasonic transducer ring-down during generation of a high-resolution position tracking of the probe. The controller can further receive a user interface command from the probe during tracking associated with the high-resolution position tracking of the probe, and present a media that corresponds to the user interface command. The media can be audio, image, video, or text.

FIG. 1 depicts an orthopedic tracking system 100 in accordance with one embodiment. The tracking system 100 comprises a probe 110, a first tracker 105, a second tracker 107, a receiver 104 and a pod 102. The probe 110 emits ultrasonic waveforms for creating a three-dimensional sensing space, a probe communication link 109 for transmitting/receiving transmission pulse data that establish a transmit time of the ultrasonic waveforms, and a user interface control (see 302 in FIG. 3) that captures a location and position of the probe 110 in the three-dimensional sensing space. The first tracker 105 and the second tracker 107 also emit ultrasonic waveforms within the three-dimensional sensing space, and include tracker communication links 106 and 108 for receiving transmission pulse data that establish a transmit time of the ultrasonic waveforms. The receiver 104 captures the ultrasonic waveforms transmitted from the probe and the two trackers 105/107 to produce captured ultrasonic waveforms. It includes a receiver communication link 103 for relaying the captured ultrasonic waveforms to the pod 102.

The pod 102 comprises a digital signal processor (see FIG. 2) to digitally sample the captured ultrasonic waveforms and track a relative location and movement of the probe 110, and two trackers 105 and 107, with respect to the receiver 104 in the three-dimensional ultrasonic sensing space from time of flight (TOF) and differential TOF waveform analysis. The pod includes a controller communicatively coupled to the probe communication link 109, the tracker communication links 106/108, and the receiver communication link 103 for synchronizing transmit and receive data functions of the digital signal processor. It also includes an I/O port 111 for communicating measurement data to a user interface associated with the relative location and the movement of the probe and the two trackers with respect to the receiver. The I/O port 111 may be a wired communication (e.g., Universal Serial Bus—USB) or wireless communication (e.g., Bluetooth or Zigbee) link. The tracker communication links 106 and 108, and the probe communication link 109 coupled to the pod 102 can also be wired or wireless.

Figure 2:
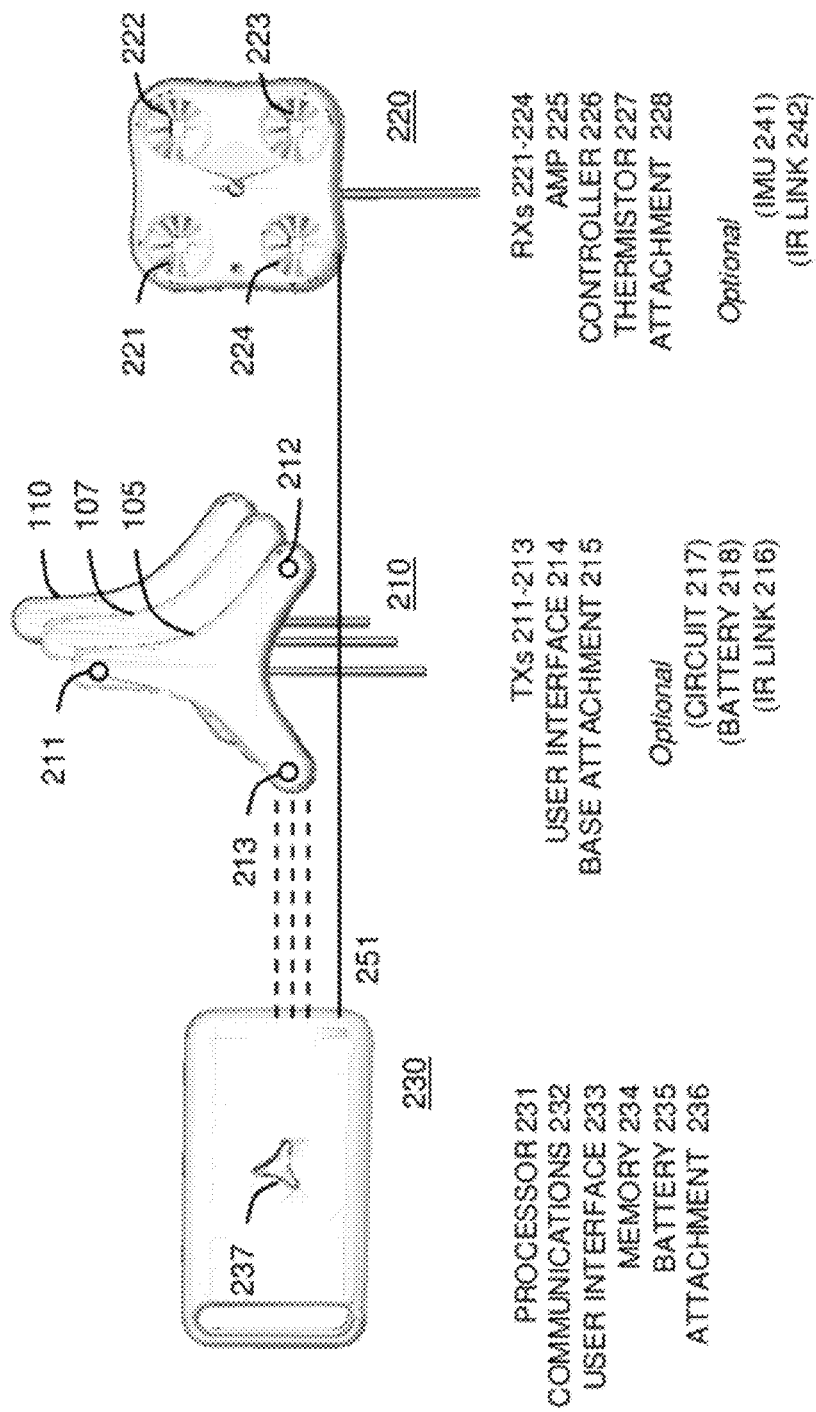
FIG. 2 depicts exemplary components of the orthopedic tracking system in accordance with one embodiment.

FIG. 2 depicts exemplary components of the orthopedic tracking system 100 in accordance with one embodiment. Components in the current figure have been renumbered from FIG. 1. As illustrated, the system 100 comprises the pod 230, the transmitters 210 (i.e., probe 110, first tracker 105 and second tracker 107) and the receiver 220. Not all the components shown are required; fewer components can be used depending on required functionality as explained ahead.

The pod 230 is communicatively coupled to the transmitters 210 and the receiver 220 over a communication link 251 (see also FIG. 1 links 103, 106, 108 and 109). In the configuration shown, the pod 230 contains the primary electronics for performing the sensory processing of the communicatively coupled sensory devices. The transmitters 210 and the receiver 220 contain minimal components for operation, which permits the sensory devices to be low-cost and light weight for mounting and handling. In another configuration, the primary electronic components of the pod 230 are miniaturized onto the receiver 220 with the battery 235; thus removing the pod and permitting a completely wireless system.

The transmitters 210 receive control information from the pod 230 over the wired connection 251 which is used for transmitting sensory signals (ultrasonic waveforms). The control information can be in the form of digital pulses or analog waveforms. Control information can be multiplexed at the pod 230 to each transmitter 210 for reducing GPIO port use. In one embodiment, the transmitter 210 comprises three ultrasonic transmitters 211-213 for each transmitting signals (e.g., ultrasonic waveforms) through the air in response to the received control information. Material coverings for the transmitters 211-21 are transparent to sound (e.g., ultrasound) and light (e.g., infrared) yet impervious to biological material such as water, blood or tissue. In one arrangement, a clear plastic membrane (or mesh) is stretched taught. The transmitters 210 may contain more or less than the number of components shown; certain component functionalities may be shared as integrated devices. One such example of an ultrasonic sensor is disclosed in U.S. patent application Ser. No. 11/562,410 filed Nov. 13, 2006 the entire contents of which are hereby incorporated by reference. Additional ultrasonic sensors can be included to provide an over-determined system for three-dimensional sensing. The ultrasonic sensors can be MEMS microphones, receivers, ultrasonic transmitters or combination thereof. As one example, each ultrasonic transducer can perform separate transmit and receive functions.

The transmitter 210 may include a user interface 218 (e.g., LED, or button) that receives user input for requesting positional information. It can be a multi-action button that communicates directives to control or complement the user interface. With a wired connection 251, the transmitters 210 receives amplified line drive signal's from the pod 230 to drive the transducers 211-213. The line drive signals pulse or continuously drive the transducers 211-212 to emit ultrasonic waveforms. In a wireless connection, the electronic circuit (or controller) 214 generates the driver signals to the three ultrasonic transmitters 211-213 and the battery 215 provide energy for operation (e.g., amplification, illumination, timing, etc). The IR Link 216 can be an IR transmitter or photodiode that communicates with respective elements of the corresponding IR link 229 on the receiver 220. The transmitter on either end device can send an optical synchronization pulse coinciding with an ultrasonic pulse transmission when used in wireless mode; that is, without wire line 251. A photo diode on the receiving end terminates the IR Link. A battery 218 can be provided for the wireless configuration if the line 251 is not available to provide power of control information from the pod 230. The communications port 216 relays the user input to the pod 230, for example, when the button of the interface 214 on one of the transmitters 210 is pressed.

The transmitters 210 by way of control information from the pod 230 can intermittently transmit ultrasonic waves from the three (3) ultrasonic transducers. The transmission cycle can vary over a 5-10 ms interval at each of the three transmitters; each transmitter takes turns transmitting an ultrasonic waveform. The ultrasonic waveforms propagate through the air and are sensed by the microphones on the Receiver 220. The system 200 can support a system polling rate; <500 Hz. The Receiver 220 determines positional information of the Wand from range and localization of transmitted ultrasonic waveforms. The system can support short range tracking of the Receiver 220 and a tracker 210 between 10 and 90 cm apart. The Receiver 220 measures the position and orientation of the tracker(s) 210 with respect to the Receiver 220 coordinate system in three-dimensions (3D) within about 120 degrees conical line of sight.

The Receiver 220 includes a plurality of microphones 221-224, an amplifier 225 and a controller 226. The microphones capture both acoustic and ultrasonic signals transmitted by the transducers 211-213 of the transmitter 210. The frequency response characteristics of the microphone permit for low Q at a transmitter 210 resonant frequency (e.g., 40, 60, 80 KHz) and also provide uniform gain for wideband acoustic waveforms in the audio range 20 to 20 KHz. The amplifier 225 amplifies the captured acoustic signals to improve the signal to noise ratio and dynamic range. It should be noted that ultrasonic signals are also acoustic signals, yet at a higher frequency than the audio range. The controller 226 can include discrete logic and other electronic circuits for performing various operations, including, analog to digital conversion, sample and hold, and communication functions with the pod 230. The captured, amplified ultrasonic signals are conveyed over the wired connection 251 to the pod 230 for processing, filtering and analysis.

A thermistor 227 measures ambient air temperature for assessing propagation characteristics of acoustic waves when used in conjunction with a transmitter 210 configured with ultrasonic sensors. An optional IR Link 229 may be present for supporting wireless communication with the transmitter 210 as will be explained ahead. An Intertial Measurement Unit (IMU) 241 may also be present for determining relative orientation and movement. The IMU 241 includes an integrated accelerometer, a gyroscope and a compass. This device can sense motion, including rate, direction and multiple degrees of freedom, including 6 axis tilt during motion and while stationary. The IMU can be used to refine position estimates as well as detection of a pivot point from pattern recognition of circular movements approximating a hemispherical surface.

The Receiver 220 responds to ultrasonic waves transmitted by the transmitters 210. It can do so in a round-robin fashion; that is, multiplex transmit signals to respective transmitters 210 to emit at specific known times and within certain timing intervals. The Receiver 220 determines positional information of the transmitter 210 from range and localization of received ultrasonic waves captured at the microphones, and also from knowledge of which transmitter 201 is pulsed. Notably, one or more transmitters 210 can be present for determining orientation among a group of transmitters 210. The pod 230 wirelessly transmits this information as positional data (i.e., translation vectors and rotational matrices) to a Display Unit. Aspects of ultrasonic sensing are disclosed in U.S. patent application Ser. No. 11/839,323 filed Aug. 15, 2007, the entire contents of which are incorporated by reference herein.

The Pod 230 comprises a processor 233, a communications unit 232, a user interface 233, a memory 234 and a battery 235. The processor 231 controls overall operation and communication between the transmitter 210 and the receiver 220, including digital signal processing of signals, communication control, synchronization, user interface functionality, temperature sensing, optical communication, power management, optimization algorithms, and other processor functions. The processor 231 supports transmitting of timing information including line drive signals to the transmitter 210, receiving of captured ultrasonic signals from the receiver 220, and signal processing for determination of positional information related to the orientation of the transmitter 210 to the receiver 220 for assessing and reporting cut angle information.

The processor 233 can utilize computing technologies such as a microprocessor (uP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system.

The electronic circuitry of the processor 231 (or controller) can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 234 may store one or more sets of instructions (e.g., software) embodying any one or more of the methodologies or functions described herein.

The communications unit 232 can further include a transceiver that can support singly or in combination any number of wireless access technologies including without limitation Bluetooth, Wireless Fidelity (WiFi), ZigBee and/or other short or long range radio frequency communication protocols. This provides for wireless communication to a remote device 104 (see FIG. 1). An Input/Output port within the communications unit 232 permits portable exchange of information or data, for example, by way of Universal Serial Bus (USB).

The memory 234 stores received ultrasonic waveforms and processing output related to tracking of received ultrasonic waveforms and other timing information, state logic, power management operation and scheduling. The battery 235 powers the processor 231 and associated electronics thereon and also the transmitter 210 and the receiver 220 in the wired configuration.

The user interface 233 can include one or more buttons to permit handheld operation and use (e.g., on/off/reset button) and illumination elements 237 to provide visual feedback.

In a first arrangement, the receiver 220 is wired via a tethered electrical connection 251 to the transmitters 210. Timing information from the pod 230 tells the transmitter 210 when to transmit, and includes optional parameters that can be applied for pulse shaping and noise suppression. The processor 231 on the pod establishes Time of Flight measurements according to the timing with respect to a reference time base in the case of ultrasonic signaling. One example of pulse shaping is taught in U.S. Pat. No. 7,414,705 the entire contents of which are hereby incorporated by reference. In a second arrangement, the receiver 220 is wirelessly coupled to the transmitters 210 via an optical signaling connection. The infrared transmitter 216 on the transmitter 210 transmits an infrared timing signal with each transmitted pulse shaped signal. The infrared timing signal is synchronized with the transmitting of the ultrasonic signals to the receiver 220. The receiver 220 can include the IR Link 229 (e.g., IR emitter or photo diode) which the pod 230 monitors to determine when the infrared timing signal is received. The pod 230 can synchronize infrared timing information to establish Time of Flight measurements with respect to a reference transmit time. The infrared transmitter and photo diode establish transmit-receive timing information to within microsecond accuracy.

Figure 3:
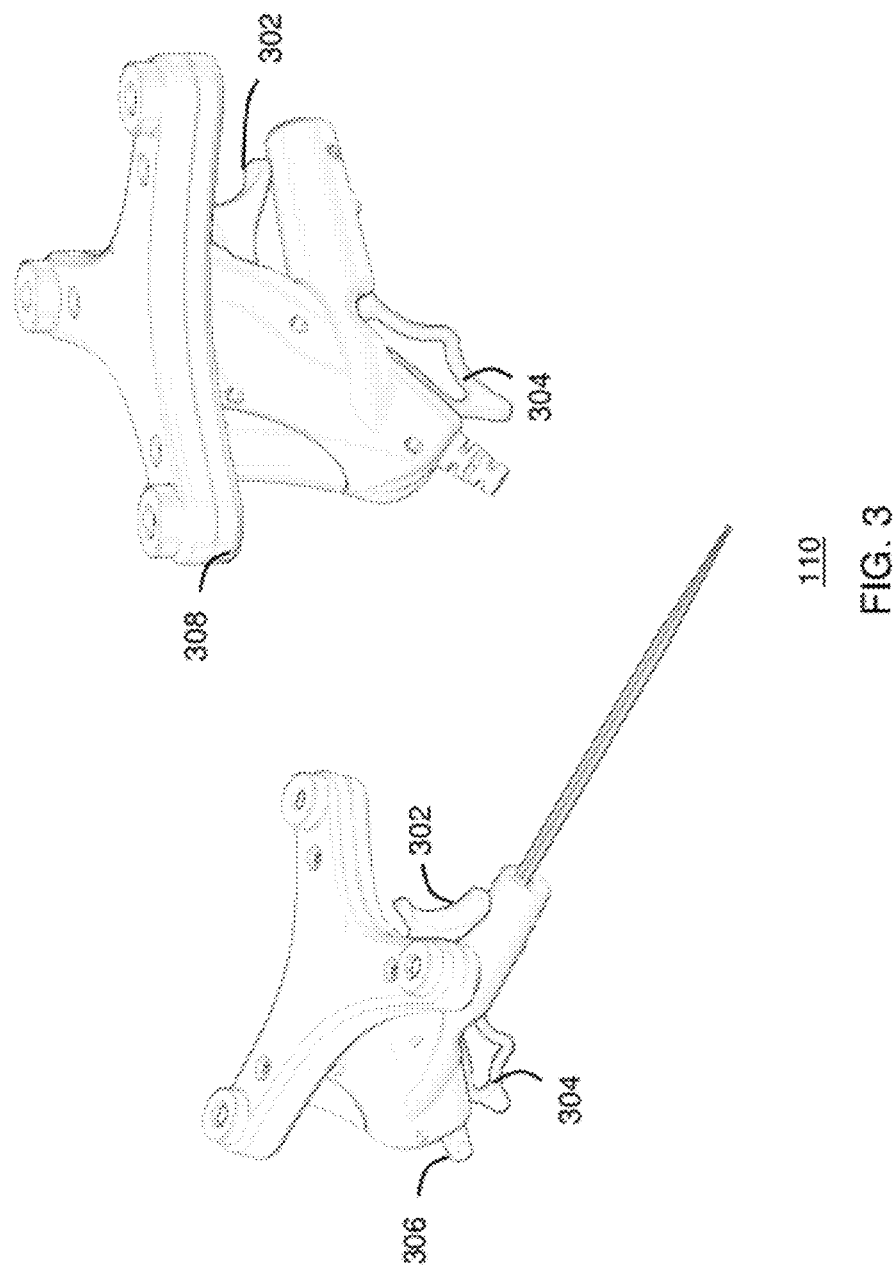
FIG. 3 depicts a probe for presenting a media responsive to a user command during an operative workflow in accordance with one embodiment.

FIG. 3 depicts the probe 110 for presenting a media responsive to a user command during an operative workflow. The probe 110 is one embodiment of the transmitter 210 shown in FIG. 2. It is configured for user control by way of a three-way switch 302. The three-way switch provides for leftward indexing, center button press, and rightward indexing. The probe also includes a release lever 304 for coupling to a probe pointer or probe plate as described above; that is, for capturing anatomical information and/or reporting geometric information. The connector 306 comprises a part of the probe communication link 109 for wired configuration. The probe also includes an illumination element 308 (e.g., LED) to convey status. As an example, the led intermittently flashes green to indicate working status, turns red in certain communication conditions (e.g., out of line of sight, communication protocol errors, etc.), and stays green when the switch 302 is activated, for example, upon capturing a landmark. Whereas the first tracker 105 and the second tracker 107 are also tracking devices (generally mounted to bones), the probe 110 provides user control to capture points or planes with respect to the location of the first tracker 105 and the second tracker 107. Aspects of GUI navigation by way of the probe 110 are disclosed in U.S. patent application Ser. No. 12/900,662 filed Oct. 8, 2010, the entire contents of which are incorporated by reference herein.

Figure 4:
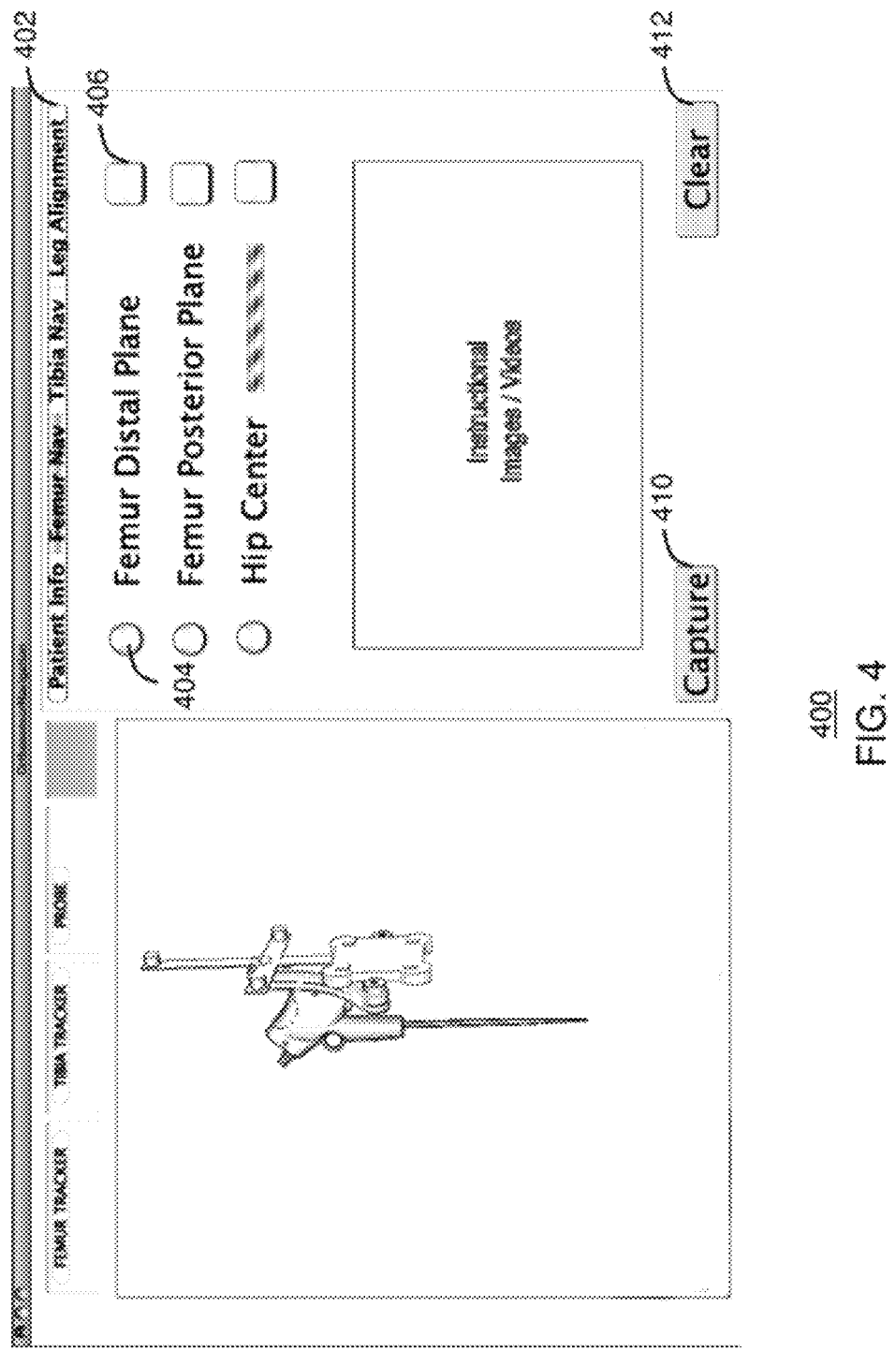
FIG. 4 depicts a graphical user interface under control of the probe in accordance with one embodiment.

Referring to FIG. 4, a graphical user interface (GUI) 400 of the orthopedic tracking system 100 is shown. The GUI 400 receives by way of the pod 102 a command from the probe 110 during high-resolution position tracking of the probe 110, and presents a media that corresponds to the user interface command. The GUI 400 exposes, or adjusts, a state of the media responsive to a pressing of the probe switch 302. The media can be at least one among audio, image, video, and text. For instance, upon the user pressing the switch 302 on the probe, the pod 102 directs a user command to the GUI 400 to alter a state of a user interface component 406. As an example, the GUI may illuminate element 404 to indicate a next operation workflow step. The user, upon placement of a probe plate onto a desired measurement area, presses the center button of the switch 302 to capture the landmark plane, and the GUI marks component 406 to indicate successful capture. The GUI 400 can automatically scroll to the next GUI element. Aspects of GUI navigation by way of the probe 110 are disclosed in U.S. patent application Ser. No. 13/164,396 filed Jun. 20, 2011, the entire contents of which are incorporated by reference herein.

During operative workflow, the user can index the three-way switch 302 left or right to navigate forward or backward over GUI components as well as pages of the tab menu 402. As illustrated, a femur nav page is displayed in the tab menu 402. Each page of the tab menu 402 is associated with an operative workflow, for example, as shown for a total knee replacement surgery. In the exemplary illustration, the tab menu 402 presents various pages (Patient Info, Femur Nav, Tibia Nav, Leg Alignment) corresponding to an operative workflow of a total knee replacement. The operative workflow and accordingly the GUI 400 can be designed specific to an orthopedic procedure (e.g., knee, hip and spine) with pages of the tab menu 402 similarly designed. The pod 102 thus presents the media according to a customized use of the probe during an operation workflow. It permits navigating a menu system of a Graphical User Interface via the tracking of the probe relative to the receiver. Furthermore, the pod 102 can recognize an operation workflow and report measurement data from the probe associated with the operation workflow. As one example, upon moving the probe (or a tracker 210) in a circular pattern the device can automatically detect femur head identification and proceed to the corresponding user component and page of the tab menu 402. Aspects of detecting a femur head are disclosed in U.S. patent application Ser. No. 12/853,987 filed Aug. 10, 2011, the entire contents of which are incorporated by reference herein. Aspects of pattern recognition using neural networks and hidden markov models in ultrasonic sensing applications for recognizing user interface gestures are also disclosed in U.S. patent application Ser. No. 11/936,777 filed Nov. 7, 2007, the entire contents of which are incorporated by reference herein.

Figure 5:
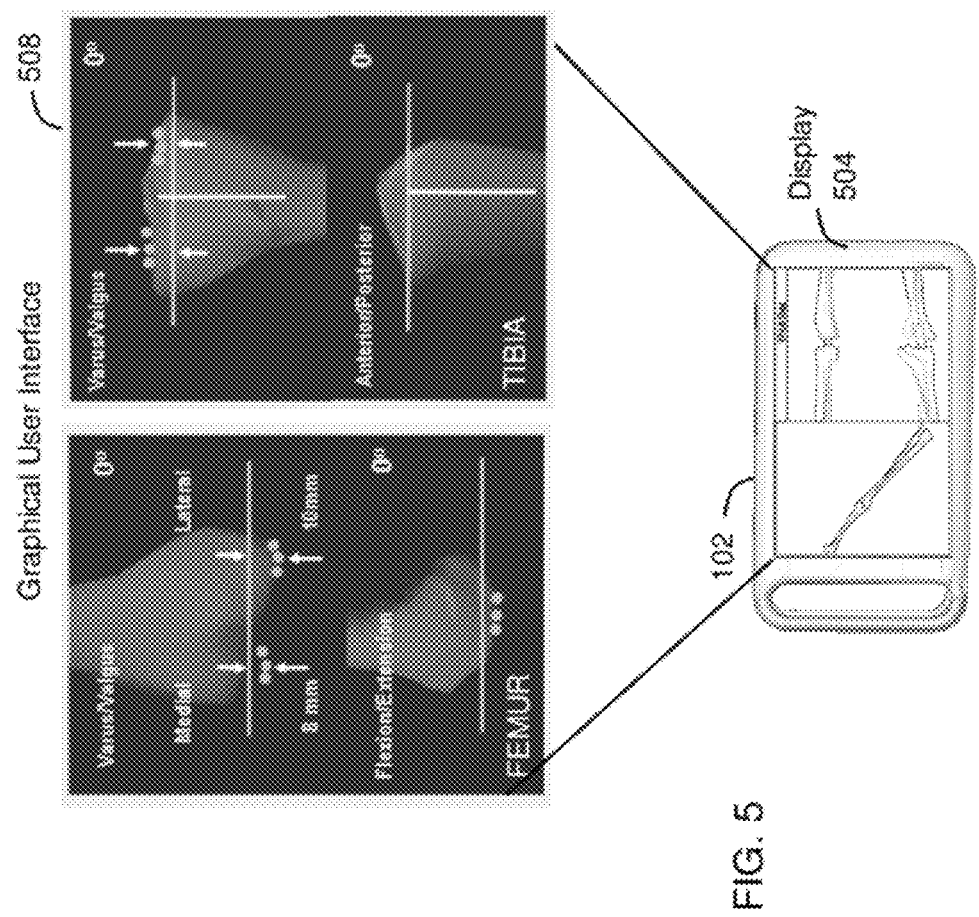
FIG. 5 depicts a graphical user interface of the orthopedic tracking system in accordance with one embodiment.

Referring now to FIG. 5, a graphical user interface 508 presenting measurement media of the orthopedic tracking system is depicted in accordance with one embodiment. As previously indicated, the pod 102 can include a display unit 504 to render 2D/3D visual information corresponding to the orientation and position of transmitters 210 with respect to the receiver 220 coordinate system, and furthermore, any devices thereto mounted. For example, as described in U.S. Provisional Patent Application No. 61/498,647, the contents of which are hereby incorporated by reference in entirety, a plate attachment can be mounted to the probe 110 to provide bone cut angle information, or a probe attachment can be thereto mounted to provide spatial position information. The plate geometry and pointer tip coordinates are stored in a memory either on the pod 102 or a communicatively coupled link station that specifically relates the plate orientation to the probe 102 orientation. Thus the orthopedic tracking system 100 can serve as a measurement device to assess anatomical cut angles and spatial distances between anatomical points.

FIG. 6A depicts communication between exemplary components of the orthopedic tracking system in accordance with one embodiment. As illustrated, the transmitter 210 emits ultrasonic waveforms by way of three or more ultrasonic transducers on a probe in a three-dimensional sensing space. The receiver 220 by way of the four microphones captures the transmitted ultrasonic waveforms. As previously noted, a thermistor on the receiver measures ambient air temperature, which the processor uses to compensate for speed of sound. Other sources of sound distortion may however be present during transmit and receiver operation of the tracking system, for example, voiced or noise signals in the operating environment. Thus, the microphones capture both ultrasonic and acoustic waveforms which are electrically converted to a combined acoustic signals. In order to remove the external acoustic waveforms from the captured signal, the processor applies noise suppression and other digital filters to isolate the ultrasonic signals from the audio and noise signals.

During transmit-receive communications between a transmitter 210 and the receiver 220, the pod 102 digitally samples captured signals which as described above may be a combination of acoustic and ultrasonic waveforms to produce sampled received ultrasonic waveforms. The pod tracks a relative location and movement of the probe in the three-dimensional ultrasonic sensing space from differential time of flight waveform analysis of the sampled received ultrasonic waveforms. For precise tracking, the ultrasonic waveforms that overlap with digitally sampled acoustic waveforms received at the microphones are first isolated as indicated above through noise suppression and filtering, and thereafter, or in conjunction with, conditioned to suppress a ringing portion of the received ultrasonic waveforms. This signal conditioning minimizes a distortion associated with ultrasonic transducer ring-down during generation of a high-resolution position tracking of the probe.

FIG. 6B illustrates signal processing functions of this communication channel in accordance with one embodiment. As illustrated, a transmit pulse 601 sent to a transmitter 210 energizes one of the three ultrasonic transducers. The transducers in response generate an ultrasonic pulse 604 that is communicated through the air. The transducer is an electromechanical system that continues to ring even upon the end of the transmit pulse 601. Certain circuit configurations (RC, RLC) can selectively dampen the ringing responsive in a predetermined manner to received control information from the pod using microphone feedback in a closed loop configuration. The resonant fine structure of the pulse 604 is periodic based on the transmit frequency (e.g., 40 to 120 KHz). On receipt at the receiver 220, the processor applies an envelope function 606 with a main lobe width 607 that compresses the pulse shape 608 to a smaller width 609 without altering the resonant fine structure. Suppression of the ringing portion of the received ultrasonic waveforms that overlap with digitally sampled acoustic waveforms minimizes distortion associated with ultrasonic transducer ring-down during generation of a high-resolution position tracking of the probe. The pod 230 applies a weighting of a Time of Flight (TOF) ultrasonic distance measurement as a function of distance between the probe and the receiver. The weighting can be applied to an envelope of a received ultrasonic waveform for selective peak amplification. The pod 230 can also apply an acoustic spherical weighting within short range of the receiver approximately between 10 cm and 90 cm. The tracking performance improvement enhances user interface functionality, and accordingly, the systems ability to predict user interface commands or motion (e.g., circular patterns, line segments, range of motion) associated with operative workflow steps for presenting media.

FIG. 7 depicts an orthopedic alignment and balance GUI in accordance with one embodiment. As shown, a first TX 210 is mounted onto the femur 311 above the femur prosthetic 341 component, and a second TX 211 is mounted on the tibia 312 below the tibia tray prosthetic 342 component. The probe 212 is used to capture anatomical landmarks on the femur for creating a femur coordinate system, and on the tibia for creating a tibia coordinate system. These established coordinate system are evaluated in real-time during range of motion of the femur and the tibia bones for reporting alignment in extension and flexion. The receiver 220 (not shown) tracks the location of the femur and accordingly the femur prosthetic 341 component from the first tracker 210, and the tibia and accordingly the tibia tray prosthetic 342 component from the second tracker 210. One example of orthopedic tracking is disclosed in U.S. patent application Ser. No. 12/764,072 filed Apr. 20, 2010 the entire contents of which are hereby incorporated by reference.

The load sensor 302 is inserted between the femur prosthetic 341 and the tibia prosthetic 342. It measures anatomical forces applied to the knee joint with respect to the cut angles and mechanical axis alignment. The alignment and balance GUI 708 measure bone cuts and applied forces thereon, for example, after prosthetics are fitted onto the bone cuts and forces thereto applied. Aspects of an integrated load balance with respect to anatomical alignment are disclosed in U.S. Provisional Patent Application No. 61/498,647 filed on Jun. 20, 2011, the entire contents of which are hereby incorporated by reference. The GUI 708 by way of the orthopedic measurement system described herein provides media presentation of orientation, positioning and distance measurements for evaluating bone resection, extension gap dynamics and soft tissue release during operative workflow.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived there from, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

These are but a few examples of embodiments and modifications that can be applied to the present disclosure without departing from the scope of the claims stated below. Accordingly, the reader is directed to the claims section for a fuller understanding of the breadth and scope of the present disclosure.

What is claimed is:

1. A portable measurement system comprising:
   a controller that emits by way of a probe ultrasonic waveforms from three or more ultrasonic transducers on a probe in a three-dimensional sensing space;
   ultrasonic transducers on a probe in a three-dimensional sensing space;
   digitally samples by way of a receiver ultrasonic waveforms from three or more microphones on a receiver to produce sampled received ultrasonic waveforms;
   tracks a relative location and movement of the probe in the three-dimensional ultrasonic sensing space from differential time of flight waveform analysis of the sampled received ultrasonic waveforms;
   suppresses a ringing portion of the received ultrasonic waveforms that overlap with digitally sampled acoustic waveforms received at the microphones;
   minimizes distortion associated with ultrasonic transducer ring-down during generation of a high-resolution position tracking of the probe, where the controller applies a weighting of a Time of Flight (TOF) ultrasonic distance measurement as a function of distance between the probe and the receiver, wherein the distance is 10 cm to 90 cm for permitting three-dimensional interaction.

2. The portable measurement system of claim 1, wherein the controller elements predicts a movement of the probe with respect to the receiver.

3. The portable measurement system of claim 1, wherein the controller element presents the media according to a customized use of the probe during an operation workflow.

4. The portable measurement system of claim 1, wherein the controller element recognizes an operation workflow and reporting measurement data from the probe associated with the operation workflow.

5. The portable measurement system of claim 1, where the controller
   receives a user interface command from the probe during tracking associated with the high-resolution position tracking of the probe; and
   presents a media that corresponds to the user interface command, wherein the media is at least one among audio, image, video, and text.

6. A portable measurement system, comprising:
   a probe comprising
      three ultrasonic transducers that emit ultrasonic waveforms for creating a three-dimensional sensing space;
      a probe communication link for receiving transmission pulses that establish a transmit time of the ultrasonic waveforms from the three ultrasonic transducers;
      a user interface control that captures a location and position of the probe in the three-dimensional sensing space;
   two trackers each comprising:
      three ultrasonic transducers that emit ultrasonic waveforms within the three-dimensional sensing space;
      a tracker communication link for receiving transmission pulses that establish a transmit time of the ultrasonic waveforms from the three ultrasonic transducers;
   a receiver comprising:
      four microphones to capture the ultrasonic waveforms transmitted from the probe and the two trackers to produce captured ultrasonic waveforms; and
      a receiver communication link for relaying the captured ultrasonic waveforms to a pod,
   the pod comprising
      a digital signal processor that digitally samples the captured ultrasonic waveforms and tracks a relative location and movement of the probe and the two trackers with respect to the receiver in the three-dimensional ultrasonic sensing space from time of flight waveform analysis;
      a controller communicatively coupled to the probe communication link, the tracker communication links, and the receiver communication link for synchronizing transmit and receive data functions of the digital signal processor
      and an I/O port for communicating to a user interface measurement data associated with the relative location and the movement of the probe and the two trackers with respect to the receiver.

7. The portable measurement system of claim 6, wherein the digital signal processor
   suppresses a ringing portion of the received ultrasonic waveforms that overlap with digitally sampled acoustic waveforms received at the microphones; and
   minimizes distortion associated with ultrasonic transducer ring-down from the probe and the two trackers during generation of a high-resolution position tracking of the probe and the two trackers.

8. The portable measurement system of claim 6, wherein the pod
   receives a user interface command from the probe during tracking associated with the high-resolution position tracking of the probe; and
   presents a media that corresponds to the user interface command, wherein the media is at least one among audio, image, video, and text.

9. The portable measurement system of claim 6, wherein the pod is communicatively coupled to a remote station via wired USB connectivity or wireless Bluetooth connectivity.

10. The portable measurement system of claim 6, wherein the probe communication link is wireless to the pod, and the tracker communication link is wireless to the pod.

11. The portable measurement system of claim 6, wherein the pod measures a position and orientation for each of the probe, first tracker and second tracker with respect to a coordinate system of the receiver in three-dimensions within about 120 degrees conical line of sight.

12. The portable measurement system of claim 6, wherein the digital signal processor applies an acoustic spherical weighting to Time of Flight (TOF) ultrasonic distance measurements as the probe moves within short range of the receiver approximately between 10 cm and 90 cm.

* * * * *